United States Patent
Colas et al.

(10) Patent No.: US 11,291,406 B2
(45) Date of Patent: Apr. 5, 2022

(54) SYSTEM FOR DETERMINING A SET OF AT LEAST ONE CARDIO-RESPIRATORY DESCRIPTOR OF AN INDIVIDUAL DURING SLEEP

(71) Applicant: UNIVERSITÉ GRENOBLE ALPES, Saint Martin d'Hères (FR)

(72) Inventors: Damien Colas, Caluire-et-Cuire (FR); Aurélien Bricout, Lyons (FR); Grégoire Gerard, Tassin la Demi Lune (FR); Pierre-Yves Gumery, Grenoble (FR)

(73) Assignee: Université Grenoble Alpes, Saint Martin d'Hères (FR)

( * ) Notice: Subject to any disclaimer, the term of this patent is extended or adjusted under 35 U.S.C. 154(b) by 122 days.

(21) Appl. No.: 16/499,827

(22) PCT Filed: Mar. 28, 2018

(86) PCT No.: PCT/FR2018/050753
§ 371 (c)(1),
(2) Date: Sep. 30, 2019

(87) PCT Pub. No.: WO2018/178569
PCT Pub. Date: Oct. 4, 2018

(65) Prior Publication Data
US 2020/0100727 A1     Apr. 2, 2020

(30) Foreign Application Priority Data
Mar. 30, 2017   (FR) ....................... 1752688

(51) Int. Cl.
*A61B 5/00*        (2006.01)
*A61B 5/024*       (2006.01)

(52) U.S. Cl.
CPC ........ *A61B 5/4818* (2013.01); *A61B 5/02405* (2013.01); *A61B 5/02416* (2013.01);
(Continued)

(58) Field of Classification Search
CPC .............. A61B 5/4818; A61B 5/02405; A61B 5/02416; A61B 5/725; A61B 2562/0204;
(Continued)

(56) References Cited

U.S. PATENT DOCUMENTS

| 4,982,738 A | 1/1991 | Griebel |
| 9,545,227 B2 | 1/2017 | Selvaraj et al. |

(Continued)

FOREIGN PATENT DOCUMENTS

| EP | 0371424 A1 | 6/1990 |
| EP | 0371424 B1 | 6/1994 |

(Continued)

OTHER PUBLICATIONS

International Search Report and International Written Opinion for International Application PCT/FR2018/050753, dated Jul. 5, 2018, 18 pages (including English translation).

(Continued)

*Primary Examiner* — Eric F Winakur
*Assistant Examiner* — Abid A Mustansir
(74) *Attorney, Agent, or Firm* — TraskBritt

(57) ABSTRACT

A system for determining a set of at least one cardio-respiratory descriptor of an individual during sleep comprises a memory device having a first accelerometer for a thoracic position, a second accelerometer synchronized with the first and for an abdominal position, and an optional sensor (e.g., a photoplethysmographic sensor). The system also includes memory for recording accelerometer and optional sensor data; memory with a reference model; and a device for filtering accelerometer data and configured to
(Continued)

extract low-, medium-, and high- frequency ranges. A computer is configured for determining, within the extracted frequency ranges, at least one characteristic representative of a cardio-respiratory and physiological state and the time of the extraction thereof; comparing the determined characteristic(s) with similar characteristics from the reference model; and deducing therefrom a set of at least one probable corresponding event the individual experienced during a predetermined period of time.

12 Claims, 2 Drawing Sheets

(52) U.S. Cl.
CPC ...... *A61B 5/725* (2013.01); *A61B 2562/0204* (2013.01); *A61B 2562/0219* (2013.01)

(58) Field of Classification Search
CPC .......... A61B 2562/0219; A61B 5/7267; G16H 50/70
See application file for complete search history.

(56) References Cited

U.S. PATENT DOCUMENTS

| | | |
|---|---|---|
| 2005/0042589 A1 | 2/2005 | Hatlestad et al. |
| 2005/0119586 A1* | 6/2005 | Coyle .................. A61B 5/4818 600/538 |
| 2007/0112286 A1* | 5/2007 | Prichard ............ A63B 69/3608 600/595 |
| 2010/0030085 A1 | 2/2010 | Rojas Ojeda et al. |
| 2011/0105915 A1 | 5/2011 | Bauer et al. |
| 2013/0060097 A1 | 3/2013 | Rubin |
| 2019/0133499 A1* | 5/2019 | Auerbach .............. A61B 5/087 |

FOREIGN PATENT DOCUMENTS

| | | |
|---|---|---|
| EP | 2621336 B1 | 7/2015 |
| WO | 2008037820 A1 | 4/2008 |
| WO | 2008096307 A1 | 8/2008 |
| WO | 2015168154 A1 | 11/2015 |

OTHER PUBLICATIONS

Fekr Atena Roshan et al., Respiration Disorders Classification with Informative Features for m-Health Applications, IEEE Journal of Biomedical and Health Informatics, vol. 20, No. 3, May 2016, pp. 733-747.

Attal Ferhat et al., Physical Human Activity Recognition Using Wearable Sensors, Sensors, vol. 15 No. 12, Dec. 11, 2015, pp. 31314-31338.

Morillo D S et al., An Accelerometer-Based Device for Sleep Apnea Screening, IEEE Transactions on Information Technology in Biomedicine, vol. 14, No. 2, Mar. 1, 2010, pp. 491-499.

Rendon David Barbosa et al, Mapping the Human Body for Vibrations using an Accelerometer, Proceedings of the 29th Annual International Conference of the IEEE EMBS, Aug. 23-26, 2007, pp. 1671-1674.

* cited by examiner

SYSTEM FOR DETERMINING A SET OF AT LEAST ONE CARDIO-RESPIRATORY DESCRIPTOR OF AN INDIVIDUAL DURING SLEEP

CROSS-REFERENCE TO RELATED APPLICATIONS

This application is a national phase entry under 35 U.S.C. § 371 of International Patent Application PCT/FR2018/050753, filed Mar. 28, 2018, designating the United States of America and published in French as International Patent Publication WO 2018/178569 A1 on Oct. 4, 2018, which claims the benefit under Article 8 of the Patent Cooperation Treaty to French Patent Application Serial No. 1752688, filed Mar. 30, 2017.

TECHNICAL FIELD

The present disclosure relates to the field of well-being, in particular, cardiorespiratory dynamic behavior while sleeping.

It is applicable to the general consumer, independently of any medical structure, for example, when a person wishes to better understand the profile of their sleep pattern and the events taking place during sleep.

BACKGROUND

The present disclosure allows an analysis of the physiology of sleep, and it is notably applicable in the collection and the analysis of data that may be used later in the establishment of a diagnosis relating to the quality of sleep. It goes without saying that the disclosed is not a diagnostic method, given that no clinical table is associated with the implementation of the latter.

The conventional methods for estimating the quality of sleep are often a compromise between cost of design/manufacture and the complexity of implementation of a device putting into practice the method, and the robustness of the analysis and hence the relevance of the evaluation.

The document EP0371424 is known. In this document, a set of sensors (heart monitor electrodes, microphone) is provided allowing an individual to be associated therewith and a plurality of signals to be recorded, such as snoring and respiration noise, together with heartbeat, during sleep in order to identify, by virtue of a calculation of indices, a potential obstructive sleep apnea.

The document EP2621336 is known. In this document, the recording of respiratory forces is provided using a pressure sensor for an awake individual and the determination of a set of parameters in order to diagnose a potential obstructive sleep apnea on the basis of an algorithm based on exhalation and the comparison of the parameters with a set of frequency bands.

The document U.S. Pat. No. 9,545,227 is known. In this document, the idea is to determine the level of risk of sleep apnea for an individual. For this purpose, the method is based on the detection of a physiological parameter converted into a preprocessed datastream from which characteristics are extracted. Using these characteristics and information from the individual, a vector is constructed in order to carry out the determination of the level of risk by comparison with a model constructed using machine learning.

Lastly, the document WO2008037820 is also known. In this document, a system is provided for acquiring and for analyzing cardio-respiratory signals characterized in that one and only one accelerometer is used for acquiring all of the physiological signals sought (heart, respiratory and snoring signals).

Thus, on the one hand, there are methods based, for example, on the analysis of signals acquired by a central processing unit of a communicating object placed on the bed of a sleeping individual.

However, aside from the fact that the components of a communicating object are not always of a quality sufficient to obtain an optimal signal for analysis, the number of physiological parameters measured is also small. Only the absence of hardware specific to the acquisition of physiological signals renders the solution inexpensive for the user, together with the development of low complexity for the designer.

On the other hand, there are medical or paramedical solutions (for example, ventilatory, polygraphic, or polysomnographic (PSG) solutions) based on a multi-modal and multi-sensor approach. Often, these methods try to analyze, via a reading in extenso of a specialist, the cardio-respiratory dynamic behavior of the individual (amongst other things) for determining the state of their sleep or identifying typical events representative of a sleep disorder. More particularly, the specialist seeks to identify the respiratory events of the obstructive or central apnea and hypopnea type. This data is usually synthesized in the form of a unique index called AHI for Apnea-Hypopnea Index and which corresponds to the sum of the events detected/unit of time, in this case an hour.

The sensors involved are typically of several types (ECG, respiratory plethysmographic, thermistance naso-buccal, etc.), mechanically increasing the cost of manufacture and of design of the solutions. The signals obtained are moreover of variable quality, not always allowing robust analysis because the individual may move during the night.

Furthermore, this multiplicity of the sensors leads to a complexity of use for the user together with a reduced acceptability since the latter has to wear all of the sensors on their torso, their fingers, their head, etc., which results in a negative influence on the quality of the sleep.

In this context, the applicant wanted to solve these problems of costs and of complexity of implementation associated with the existing solutions, while at the same time conserving a very good robustness of analysis.

Accordingly, the solution provided here consists of an approach based, for example, on a pair of accelerometers carried on board the same hardware device disposed at a single location on the individual on the trunk of the individual, which makes the disclosed systems practical, compact and easy to implement. With the aim of improving the robustness of the measurements described hereinafter, a set of at least one additional sensor may furthermore be incorporated, chosen from amongst a photoplethysmographic sensor (PPG), which allows an indirect optical measurement of the oxygenation of the blood and the heart beat; a microphone and a gyroscope, allowing the angular position of the device to be followed.

Aside from the technological advances provided by the present disclosure, the latter meets a double need for public health and for medical practice: certain populations are not aware of their sleep disorders and, as a consequence, are not oriented in the direction of good health. The present disclosure can enable these populations to be detected and may accordingly allow a public health need to be met, since it allows a, potentially early, diagnosis on these populations. Moreover, the standard techniques (PSG) require expertise that is complicated to obtain and to practice and thus limit the number of experts available. The present disclosure allows the sharing with non-specialist professionals of an accurate tool for the evaluation of cardio-respiratory health during sleep to be promoted.

BRIEF SUMMARY

More precisely, the disclosure relates to a system for determining a set of at least one cardio-respiratory descriptor of an individual during sleep.

The system is essentially characterized in that it comprises:
a measurement device comprising:
  a first set of at least one accelerometer, configured so as to be placed in a thoracic position on the individual; and
  a second set of at least one accelerometer, synchronized with the first set of at least one accelerometer and configured so as to be placed in an abdominal position of the individual; and
  optionally, at least one from amongst a photoplethysmographic sensor (PPG), a microphone and a set of at least one gyroscope synchronized with the first set of at least one accelerometer;
a memory for recording the data coming from the accelerometers and from the optional sensors;
a reference model recorded in a memory, the model comprising a correspondence between a set of characteristics distributed over time and a set of given physiological events, each event being preferably representative of a potential sleep disorder;
a device for filtering the data coming from the accelerometers configured for extracting low frequency, medium frequency and high frequency ranges, and
a computer configured for:
  determining, within at least one of the extracted ranges of frequencies, a set of at least one characteristic representative of a cardio-respiratory and physiological state, together with the time at which the characteristic was extracted;
  comparing the set of at least one determined characteristic with similar characteristics coming from the reference model, and
  deducing therefrom a set of at least one probable corresponding event which the individual experienced during a predetermined period of time.

The device for filtering the data may be configured for:
extracting a low-frequency range, a medium-frequency range and a high-frequency range of the data coming from the first set of at least one accelerometer, and
extracting at least one low-frequency range of the data coming from the second set of at least one accelerometer.

The following may furthermore be provided:
means for determining the position of the individual during sleep, from the data coming from at least one from amongst the first set of at least one accelerometer and the second set of at least one accelerometer; and
the computer being configured for determining, based on at least one from amongst the events, a set of at least one cardio-respiratory descriptor of the individual.

At least one of the sensors may furthermore be provided from amongst:
a photoplethysmographic sensor (PPG),
a microphone and
a set of at least one sensor for measuring angular position, synchronized with the first set of at least one accelerometer and configured so as to be placed in a thoracic position on the individual;
the device for filtering the data being furthermore configured for:
coupling the data from a set of at least one sensor for measuring angular position with the data from at least one from amongst the first set of at least one accelerometer and the second set of at least one accelerometer, for the extraction of characteristics on position of the user or on atypical variations in respiratory angular speed; and/or
averaging the data coming from the optical photoplethysmographic sensor.

The computer may be configured for determining a set of at least one cardiorespiratory descriptor of the individual from amongst:
an apnea-hypopnea index (AHI),
a first set of respiratory forces in the data coming from the first set of at least one accelerometer,
a second set of respiratory forces in the data coming from the second set of at least one accelerometer,
a thorax-abdomen desynchronization index, by synchronized comparison of the first set of respiratory forces and of the second set of respiratory forces,
the heart rate variability (HRV),
the oxymetric profile or oxygen saturation,
the respiratory entropy per unit time,
the percentage of snoring per unit time; and
a night-time profile of the oxygen saturation.

For example, the percentage of snoring per unit time is determined, at least in part, as a function of the data coming from at least one from amongst the first set of at least one accelerometer and the microphone.

For example, the night-time profile of the oxygen saturation is determined, at least in part, as a function of the data coming from the thoracic PPG sensor.

The computer may be configured for selecting a set of characteristics from amongst the set of determined characteristics, for example by an algorithm of the Sequential Feature Selection (SFS) or Fast Correlation-Based Filter (FCBF) type, prior to the comparison.

The computer may be configured for calculating at least one from amongst:
the temporal correlation between at least two events identified over the same range of time or over several ranges of time;
a set of (event/position) pairs,
a set of (event/characteristic) pairs,
a set of (event/characteristic/position) triplets, and
a set of (event/event/characteristic/position) quadruplets.

The computer may be configured for identifying a chain of events that, during a predetermined time window, resulted in a cardio-respiratory descriptor of abnormal value.

Means may furthermore be provided for enabling/disabling the accelerometers and optional sensors.

It may be provided for the memory for recording the data coming from the accelerometers and from the optional sensors and the memory for recording the reference model to be the same; the memory being either:
remote, or
connected via a data link with the first set of at least one accelerometer, the second set of at least one accelerometer and also with the optional sensors.

Other characteristics and advantages of the present disclosure will become more clearly apparent upon reading the following description given by way of nonlimiting example and with reference to the accompanying figures.

DETAILED DESCRIPTION

By convention of language, the terms "individual," "subject" or "user" refer to a physical person user of a measuring device according to the present disclosure.

The term "sleep" is understood to mean a period of time, potentially variable, during which the measuring device according to the present disclosure is active; the individual normally being asleep, potentially in a discontinuous manner, during at least a part of this period of time.

Measuring Device

A single compact measuring device is provided comprising at least two accelerometers.

In particular, a first set of at least one accelerometer is provided, intended to be placed in a thoracic position on the individual, preferably in a xiphoidal position, which allows the cardiac mechanical activity, the thoracic ventilatory forces and the snoring activity to be measured.

A second set of at least one accelerometer is also provided, intended to be placed in an abdominal position on the individual, which allows the ventilatory forces of the abdomen to be measured.

Each set of at least one accelerometer may comprise a plurality of accelerometers, for example for reasons of redundancy and robustness.

In this case, tests carried out by the applicant have demonstrated that a single accelerometer per set can suffice.

Furthermore, the addition of other optional sensors may also be provided, for example at least one from amongst a photoplethysmographic sensor, hereinafter PPG sensor, and a microphone, in this case placed in a xiphoidal thoracic position. A set of at least one sensor for measuring angular position may also be provided, here a gyroscope, in combination with a set of at least one accelerometer.

As a consequence, the measuring device illustrated here notably comprises two accelerometers, and, for concision, the first set of at least one accelerometer is referred to as first accelerometer 110, and the second set of at least one accelerometer is referred to as second accelerometer 120.

Each sensor (for example, accelerometer) emits a respective signal comprising a set of data. For concision, "signal" and "data" are therefore understood to mean the same thing.

Preferably, it is provided for the measuring device to comprise means of enabling/disabling the sensors, for example in the form of an analog or digital enabling control switch.

Figure 1:
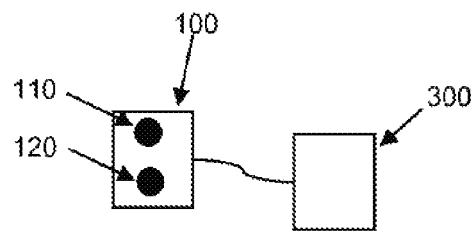
FIG. 1 illustrates one embodiment of the system according to the invention present disclosure.
Figure 2A:
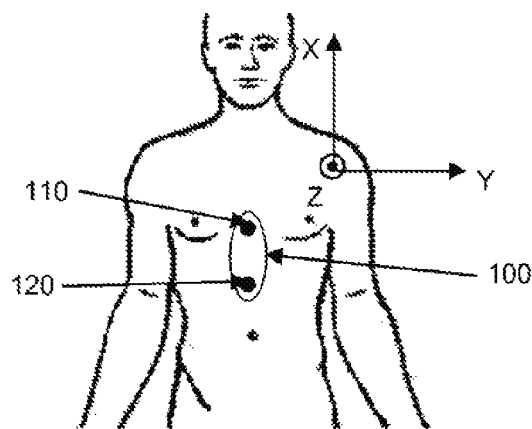
FIG. 2A illustrates one mode of positioning of the accelerometers and of the optional sensors according to the present disclosure.

In a first variant, illustrated in FIG. 2A, the first accelerometer, the second accelerometer and the optional sensors are rigidly attached to a single support 100.

Figure 2B:
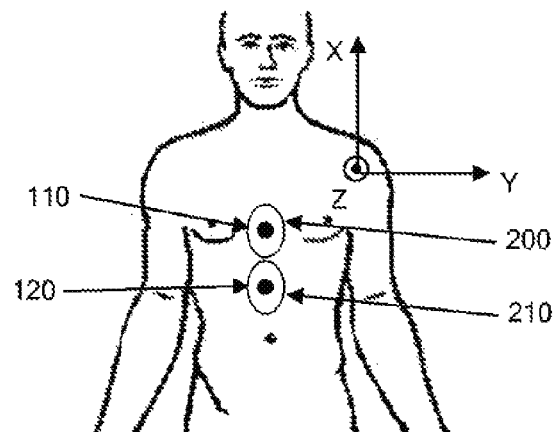
FIG. 2B illustrates another mode of positioning of the accelerometers and of the optional sensors according to the present disclosure.

In a second variant, illustrated in FIG. 2B, it is provided for the first accelerometer and the second accelerometer to be rigidly attached to a respective support 200, 210. The optional sensors may be rigidly attached to the support of the first set of at least one accelerometer.

Irrespective of the variant, each support comprises an upper face and a lower face. The upper face carries at least one accelerometer and the lower face is typically coated with an adhesive (glue), preferably re-positionable. The advantage of the repositionable aspect is that the individual can remove the measuring device upon waking and re-use the same measuring device the following night, and over several consecutive days. The device is, for example, powered by a battery.

The first accelerometer and the second accelerometer may be identical. Here, the first accelerometer and the second accelerometer are standard three-axis accelerometers, here with X the length-wise axis of the individual and the axis Z which is orthogonal to the subject (FIGS. 2A and 2B).

The sets of data coming from each sensor are recorded in a computer memory.

In a first variant, the memory is connected via a data link with the first and the second accelerometer and also with the optional sensors. The memory may, for example, be disposed on the single support or any one of the supports for the accelerometers.

Preferably, it is provided for the memory to be connected via a data link with an input/output (I/O) communications port, for example a USB port, which allows the recorded data to be exported to a data processing device comprising a data processing software application, typically any communicating object, in other words an electronic device comprising wired or wireless communications means, a computer 300 (processor) and preferably a display screen, for example a personal computer, a smartphone, a touch-screen tablet, etc.

It may also be provided for the memory to be removable, for example in the form of a data medium of the USB memory stick type, connectable to the first accelerometer and to the second accelerometer for the recording of the data coming from the latter, and subsequently connectable to a computer with a filtering software application allowing the data to be filtered.

In a second variant, the memory is remote, in other words with no wired connection between the memory and the sensor. For example, the memory is located remotely in the data processing device.

In this case, the measuring device advantageously comprises means of communication with the data processing device, whether this be a wired or wireless communication.

The memory may therefore be onboard or remote, on a server, in particular of a cloud data storage system.

The accelerometers and the optional sensors are advantageously installed on an electronic board, comprising a battery, a computer, for example a processor (microcontroller) and a storage unit able to store the data with the aim of onboard processing. Alternatively, each accelerometer is mounted on an independent electronic board, each disposing of a power supply battery, of a computer (processor) and of a storage unit. The optional sensors are rigidly attached to the electronic board of the first set of at least one accelerometer. The synchronization of the signals is effected by construction by the microcontroller.

Preferably, means of processing the signals coming from the sensor are also provided.

In this case, the means for processing the signals comprise filtering means, configured for filtering the output signal from the first accelerometer, and configured for filtering the output signal from the second accelerometer.

In a manner similar to the memory, the filtering means may be integrated into the measuring device, or located remotely on the data processing device or else in a server in communication with the data processing device.

In this case, the measuring device advantageously comprises means of communication with the signal processing means, whether this be a wired or wireless communication.

The photoplethysmographic sensor comprises an optical transmitter and receiver allowing the oxygen saturation of the blood to be measured in the thorax by the difference in absorption between hemoglobin and oxy-hemoglobin between red and infrared light.

Each signal generated by the accelerometers is processed in order to render it exploitable, then analyzed over several frequency bands in order to extract from it various values of physiological parameters likely to indicate the occurrence of events typical of sleep respiratory disorders, hence affecting the quality of sleep, as described hereinafter.

Processing of the Data

Processing of the data coming from the accelerometers is provided in the following manner.

The measuring device is installed on the individual, preferably by the latter, before going to bed, for continuous operation.

Raw Data

The data sets coming from the first accelerometer and from the second accelerometer are referred to as raw data.

The raw data is filtered as described hereinbelow, either after having been recorded in the memory or on the fly.

By way of non-limiting example, the raw data supplied by the accelerometers is preferably sampled at a frequency of 10 KHz.

By way of non-limiting example, the raw data supplied by the PPG sensor is preferably sampled at a frequency of 25 Hz.

Advantageously, the acquisition is carried out continuously over the entire duration of the sleep phase.

Filtered Data

Figure 3:
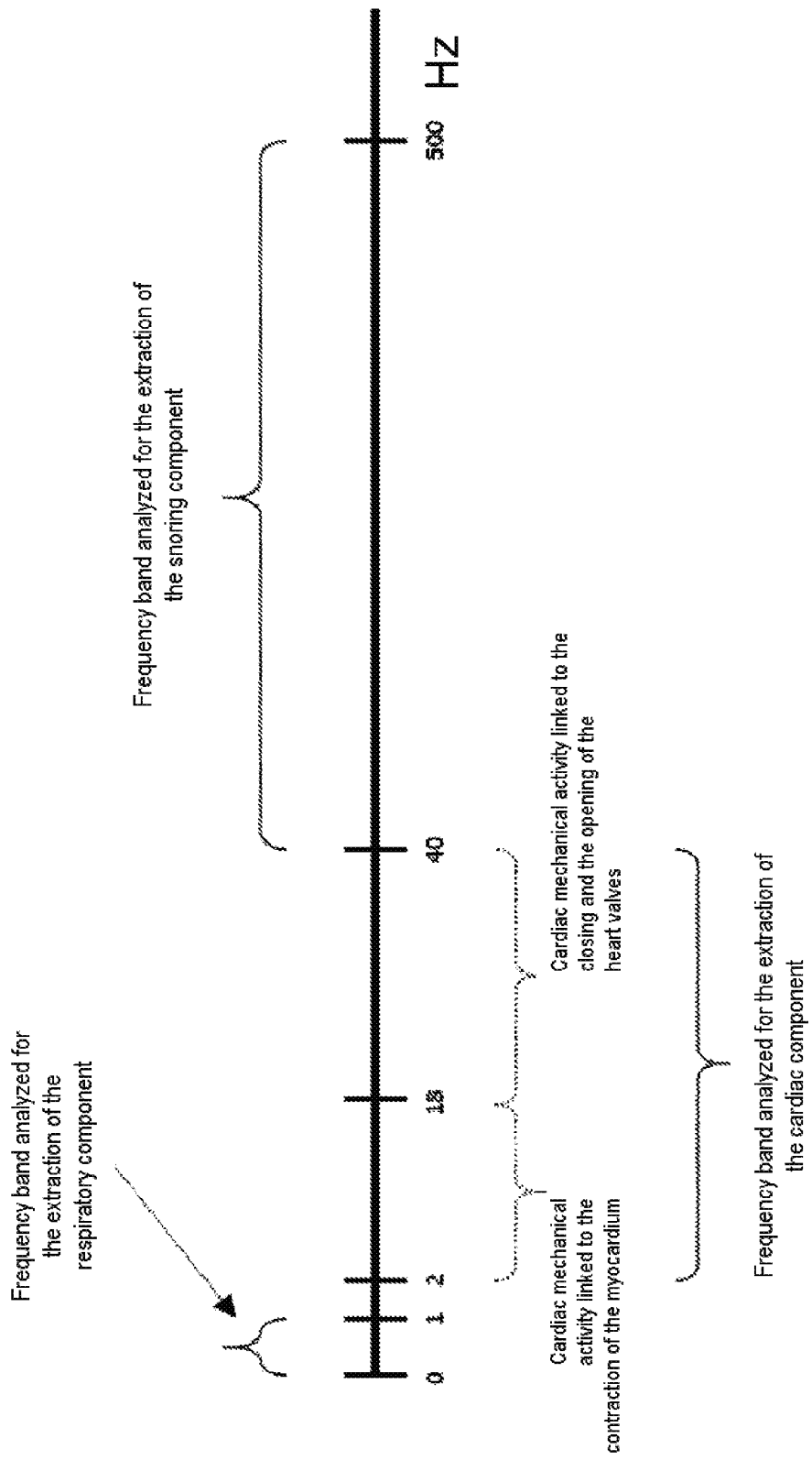
FIG. 3 illustrates the ranges of frequencies according to the present disclosure.

The accelerometers have a frequency bandwidth preferably included in the range from 0 to 500 Hz, illustrated in FIG. 3.

Typically, the range of frequencies hereinabove may be subdivided according to the following ranges and correspondence:
the range from 0 to 1 Hz, hereinafter "low-frequency" range, corresponds to respiratory activity of the individual,
the range from 2 to 40 Hz, hereinafter "medium-frequency" range, corresponds to cardiac activity of the individual; it may be subdivided into:
 a sub-range from 2 to 18 Hz which corresponds to mechanical cardiac activity associated with the contraction of the myocardium of the individual, and
 a sub-range from 18 to 40 Hz which corresponds to mechanical cardiac activity linked to the closing and to the opening of the heart valves of the individual, and
the range from 40 to 500 Hz and beyond, hereinafter "high-frequency" range, corresponds to snoring activity of the individual.

The low-frequency range is the respiratory component of the signal from an accelerometer; it is caused by the movements of the thorax of the individual while breathing.

The medium-frequency range is the cardiac component of the signal from an accelerometer; it is caused by the cardiac activity of the individual.

The high-frequency range is the snoring component of the signal from an accelerometer; it is caused by the vibrations due to the snoring of the individual.

Each of the activities of the individual (respiratory, cardiac and snoring) accordingly make the accelerometer or accelerometers vibrate according to a specific and exclusive range of frequencies.

A filtering step is therefore advantageously provided that consists in filtering the signals coming from the accelerometers in order to extract from the signals at least one of the components, or equally bands or ranges, from amongst the "low frequencies," the "medium frequencies" and the "high frequencies."

In this case, the following are extracted:
the respiratory component by any known low-pass filter, and, for example, by principal component analysis (PCA) or by discrete Fourier transform;
the cardiac component by any known band-pass filter, and, for example, by adaptive filtering, by envelope extraction, by learning, by cross-correlation, by partitioning into k-averages, or principal component analysis (PCA), and
the snoring component by any known high-pass filter, and, for example, by spectral analysis.

Preferably, the respiratory component, the cardiac component and the snoring component are extracted from the raw data coming from the first accelerometer, placed in a thoracic position on the individual.

Preferably, at least the respiratory component is extracted from the raw data coming from the second accelerometer placed in an abdominal position on the individual.

Advantageously, with a disposition of three-axis accelerometers X, Y and Z such as illustrated in FIGS. 2A and 2B, with XoZ the sagittal or median plane, XoY the coronal or frontal plane and YoZ the axial or transverse plane, the following may be extracted:
the respiratory component by a linear combination of the three axes, here in the form of a vector;
the cardiac component using only the component along the axis Z of the signal from each accelerometer,
the snoring component by a linear combination of the three axes, here in the form of a vector.

Weighting of the snoring component extracted along at least one of the axes X, Y and Z in an adaptive manner may furthermore advantageously be provided, as a function of the position of the individual; the determination of the position of the individual is described hereinbelow.

A step for smoothing the signals after extraction of the components in each of the frequency bands may also be provided, which allows artifacts to be removed.

In the PPG sensor, the difference in absorption is calculated between hemoglobin and oxy-hemoglobin between red and infrared light. An averaging filter is subsequently considered with an intermediate averaging time allowing a compromise between precision of measurement and artifact rejection. This time is, by way of nonlimiting example, equal to 1 second.

Synchronization

The (raw or filtered) data coming from the second accelerometer is synchronized with the (raw or filtered) data coming from the first accelerometer and the data from the optional sensors, for example by a computer (processor), onboard computer (microcontroller) or an acquisition system (server).

For example, an acquisition system may be provided, in this case a CPU or a microcontroller, coupled to a clock and a sampler and an analog-digital converter.

As described hereinbelow, the position of the individual may be determined during sleep. This position may be synchronized with the determined characteristics (respiratory, cardiac, snoring), as described hereinbelow.

Determination of Characteristics

Using data coming from the accelerometers (raw and, preferably, filtered) and furthermore, where present, from at least one amongst a PPG sensor, a microphone, and a set of at least one gyroscope, it is possible to determine, by frequency band, a set of at least one characteristic representative of a sleep disorder normally taking place in a sleeping phase of the individual, together with the time, in other words the moment in time or the period of time, at or during which the characteristic was extracted.

Indeed, sleep respiratory disorders correspond to physical or physiological conditions of the individual: snoring, tossing and turning, positioning of the individual, thoracic respiration (or absence thereof), abdominal respiration (or absence thereof), etc. The convergence of these events may point toward a potentially pathological state.

These physical or physiological conditions correspond, in turn, to measurable characteristics, which are extracted from the signals coming from the accelerometers and, where present, from the optional sensors.

The "low-frequency" range of the accelerometers is representative of respiratory forces, which comprise, for example, the inhaling and the exhaling of the individual.

Characteristics may be extracted from this, such as:
the respiratory frequency, in other words both the thoracic respiratory frequency and the abdominal respiratory frequency,
the respiratory amplitude,
the respiratory entropy,
etc.

The "medium frequencies" range is representative of the contractions of the heart of the individual.

Characteristics may be extracted from this, such as:
the instantaneous heart rate, by virtue of at least the first accelerometer,
the time between two successive heart beats,
etc.

The "high frequencies" range is representative of the snoring episodes of the individual.

Characteristics may be extracted from this, such as:
the snoring times or frequency of the individual, by virtue of at least the first accelerometer,
the spectral analysis of snoring (power, amplitude, etc.), etc.

For the optional sensors, provision is made for extracting characteristics representing the oxygen saturation of the individual in the thorax by virtue of the PPG sensor.

Based on at least one from amongst the first accelerometer, the second accelerometer and at least one angular position sensor, typically a gyrometer (or equally a gyroscope), angular position characteristics may be extracted allowing preferably an algorithmic optimization for:
The calculation of the position of the user,
The detection, in association with at least one set of accelerometers, of potential abnormal respiratory patterns (atypical angular variation when respiration is recovered post-obstructive apnea, for example).

The "low frequency," "medium frequency" and "high frequency" ranges may be processed in series or in parallel.

Furthermore, the selection of a set of characteristics may also be provided from amongst the set of determined characteristics, in particular by an algorithm of the Sequential Feature Selection (SFS) or Fast Correlation-Based Filter (FCBF) type, which allows the calculations to be optimized.

Sleep Disorders—Events

The sleep disorder of the individual is notably characterized by at least one of the syndromes from between:
obstructive sleep apnea syndrome (OSAS), and
central sleep apnea syndrome (CSAS).

These syndromes typically correspond to the occurrence of at least one of the following (physiological) events during the sleep of the individual:
an obstructive apnea,
a central apnea,
a mixed apnea,
a hypopnea,
a hyperventilation and
a hypoventilation.

The events hereinabove may be characterized by a specific distribution over time of the determined characteristics.

From a physiological point of view, in the majority of cases of OSAS, the air stops flowing in the direction of, and from, the lungs because of a blockage in the upper airways, in the nose or in the throat.

As opposed to OSAS, CSAS can occur even when the airways are clear. CSA means that the individual stops breathing for a predetermined number of consecutive seconds during sleep, in this case at least 10 consecutive seconds.

Hypopnea, or superficial respiration, on the other hand, is a decrease in the respiratory flow rate, whose limits are more or less well defined, for a predetermined number of consecutive seconds during sleep. Here, it is considered that a reduction of at least 50% in the respiratory flow rate for 10 seconds defines a hypopnea. Hypopnea may furthermore be defined with a decrease of 3% to 4% in saturation (oxygen in the blood).

In practice, apnea/hypopnea may therefore be characterized by repeated interruptions of respiration or weak respiration for short periods of time during sleep. In anatomical terms, there is an intermittent collapse of the upper airways which may possibly correspond to a reduction in the concentrations of oxygen in the blood during sleep. Thus, a sleeping person becomes incapable of breathing normally and usually wakes up with each collapse.

In reality, these definitions are relative and the limits are not clearly established due to the different definitions depending on the authors and to the absence of harmonization. In other words, two different experts, when faced with the same results, may offer two different interpretations, including, for example, by taking into account or not factors relating to the individual (risk factors, medical antecedents, etc.) in their diagnosis.

The present disclosure allows these restrictions to be avoided.

Reference Model

A reference model is provided. Here, the reference model comprises a first group of physiological data relating to individuals recognized as being afflicted with a sleep disorder, for example a set of polysomnographs.

The reference model also advantageously comprises a second group of physiological data, relating to individuals recognized as not being afflicted with a sleep disorder, for example a set of polysomnographs.

In particular, it is provided for at least the first group of physiological data to comprise a correspondence between a set of characteristics distributed over time and a given event (obstructive apnea, central apnea, mixed apnea, hypopnea, hyperventilation or hypoventilation).

It is then possible to compare the (determined or selected) characteristics with the reference model, here at least with the data of the first group, in order to deduce therefrom the probable corresponding event or events which the individual experienced during the period of time in question, which allows a set of events that are potentially indicators of a sleep disorder to be detected and a form of screening for sleep disorder to be carried out instead of a diagnosis which, for its part, aims to identify the nature and the cause of the disorder with which a patient is afflicted.

Preferably, the comparison step is implemented by machine learning, which consists in constructing a decisional model, for example by a support vector machine (or SVM), by a Gaussian approach, by a Bayesian approach, etc., notably for the detection and discrimination of abnormal respiratory events.

The comparison is made, for example, on the following extracted characteristics:
respiratory (frequency, amplitude, thoraco-abdominal synchronization index),
cardiac (heart rate, HRV),
snoring (spectral composition),
thoracic oxygen saturation (PPG sensor).

The learning within the processing of the signals coming from the first and second accelerometers allows the characteristics extracted to be rendered more robust and hence the performance of the comparison algorithm to be improved. For example, the processing of the signal coming from the "medium-frequency" range must result in a sufficiently precise heart rate.

Here, the comparison step is implemented by learning supervised by the reference model.

Classification and Determination of Cardio-Respiratory Descriptors

Based on the determined characteristics representative of a potential sleep disorder, a set of at least one cardio-respiratory descriptor of the individual may be determined, each descriptor being representative of the occurrence of event(s) representative of sleep disorder(s) while the individual is sleeping; in other words, the type of disorder (apnea, hypopnea, hyper- or hypoventilation), the time at which the event occurs, and the number of times where these events take place, together with their frequency if they are regular.

A typical cardio-respiratory descriptor is, for example, AHI, calculated based on the number and on the type of respiratory events detected per hour of sleep (obstructive, central or mixed apneas/obstructive or central hypopneas).

Another cardio-respiratory descriptor is the thorax-abdomen desynchronization index per unit time. The latter allows the central or obstructive nature of the apneas to be refined.

In this case, the respiratory forces coming from the filtered data of the second (abdominal) accelerometer and the respiratory forces coming from the filtered data of the first (thoracic) accelerometer may be compared. The thorax-abdomen desynchronization index is calculated by an estimation of the phase shift between the signals coming from the first accelerometer and the signals coming from the second accelerometer. The delay of one with respect to the other may then be estimated by comparison of their respective passages through 0, then by the calculation of a transform into wavelets for comparison of the spectral phase.

Another cardio-respiratory descriptor is heart rate variability (or HRV), which is the fluctuation of the duration of the intervals of time between two consecutive heart beats.

It essentially results from extrinsic regulations and determines the heart rate. While the heart rate may be quasi-stable over a given time integration period, the time between two heart beats may be very different and its informative value is greater.

In this case, the extraction of the cardiac component furthermore comprises a step for determining the variability of the heart rhythm, here by temporal and spectral analysis of the signal from the first accelerometer in the "medium-frequency" range.

Another cardio-respiratory descriptor is the oxygen desaturation index over the measurement night. It reports the desaturation number greater than 3% over the night, the highest oxygen desaturation over the night and the average profile over the night.

Another cardio-respiratory descriptor is respiratory entropy per unit time.

Another cardio-respiratory descriptor is the percentage of snoring per unit time.

Advantageously, at least one of the cardio-respiratory descriptors determined is coupled to the position of the individual. The occurrence of events indicative of sleep disorder, identified by the comparison step, may indeed be associated with the position of the individual, at that time or within a predetermined preceding time window, which allows cardio-respiratory descriptors to be determined for which the physiological data of the individual are coupled to their posture in a synchronized manner.

The following may thus, for example, be determined:
a set of pairs: snoring/position; HRV/position; snoring/heart rate; HRV/heart rate; etc.
a set of triplets: snoring/heart rate/position; etc.
a set of quadruplets: snoring/heart rate/HRV/position; etc.

The chain of events may thus be more easily identified which, during a predetermined time window, resulted in an abnormal cardio-respiratory characteristic, for example an increase in heart rate, an increase in the amplitude of snoring, etc. In order to determine whether a cardio-respiratory characteristic is "abnormal," the value of the characteristic is typically compared with a reference value, preferably included in the reference model.

In addition to the identified or selected events, the decisional model may use as input other information relating to the individual, including but not limited to: their age, their weight, their height, the circumference of their neck, their medical antecedents, their nutritional habits, their consumption of products recognized as capable of interfering with sleep (notably alcohol and cigarettes).

The calculation may also be carried out of the temporal correlation between at least two physiological events of the individual over the same period of time (simultaneity of the events) or over several periods of time (diachronism of the events, for example turning onto a side that induces snoring).

Determination of Position

The determination of the position of the individual during sleep is subsequently carried out by quantification of the variations of acceleration along the various axes. Typically, the signals coming from at least one of the accelerometers and, optionally, from a set of at least one gyroscope allow it to be determined whether the individual is in one of the positions from amongst:
lying on their back,
lying on their belly,
lying on their right side,
lying on their left side,
sitting or half-sitting, and
standing.

By virtue of the present disclosure, it then becomes possible to perform a statistical analysis by cross-correlation, which allows the conditions in which the individual suffers from sleep disorder to be better defined, for example an accelerated heart rate when they are snoring on their left side.

The data coming from the first and second accelerometers and, where relevant, from the additional optional sensors are analyzed (in real time or a posteriori) by a succession of sliding windows whose duration is predetermined (for example, a few seconds) over a predetermined total period (for example, a few minutes) and the characteristics determined during this predetermined total period are compared with the data of the reference model.

The data coming from the first and second accelerometers, from the PPG sensor, from the microphone or the position of the individual, may also be used as a discriminator for the identified or selected events. For example, an accelerated heart rate associated with a vertical acceleration indicates that the individual is certainly getting up, hence awake, and the corresponding events may then be discriminated from the step for comparison with the reference model.

By virtue of the present disclosure, it is possible to obtain dynamic behavior of the measurements over several nights whereas the prior art only allows a single night.

The time for analysis according to the solutions of the prior art is generally of the order of one to two hours of work in order to analyze one night for an individual. In contrast, according to the present disclosure, the calculation time is that of a computer (processor), i.e., a few seconds. Furthermore, the calculation is automatic, in other words independent of any human intervention, in particular of medical specialist intervention.

The present disclosure allows the identification of correlated and abnormal events, such as the monitoring of treatment for sleep disorders. It is non-intrusive, does not require any conventional bulky equipment (headset, EEG, EMG, oxygenation or air flow measuring device, etc.) and may only require two accelerometers, for a measurement and analysis precision adapted to the procedure for early diagnosis in the general population or the diagnosis of pathology.

The invention claimed is:

1. A system for determining a set of at least one cardio-respiratory descriptor of an individual during sleep, comprising:
   a measuring device comprising:
      a first set of at least one accelerometer, configured so as to be placed in a thoracic position on the individual; and
      a second set of at least one accelerometer, synchronized with the first set of at least one accelerometer and configured so as to be placed in an abdominal position on the individual;
   a first memory for recording data coming from the accelerometers;
   a reference model recorded in second memory, the reference model comprising a correspondence between a set of characteristics distributed over time and a set of given physiological events, each given physiological event preferably being representative of a potential sleep disorder;
   a set of at least one gyroscope for measuring angular position, synchronized with the first set of at least one accelerometer and configured so as to be placed in another thoracic position on the individual; and
   a computer configured for:
      determining, within at least one of an extracted frequency range, a set of at least one characteristic representative of a cardio-respiratory and physiological state, together with the time at which the characteristic was extracted;
      comparing the set of at least one determined characteristic with similar characteristics coming from the reference model; and
      deducing therefrom a set of at least one probable corresponding event which the individual experienced during a predetermined period of time; and
   filtering means for filtering the data coming from the accelerometers, the filtering means being configured for:
      extracting from data coming from the first set of at least one accelerometer:
         a low-frequency range, within a range from 0 Hz to 1 Hz, which corresponds to respiratory activity of the individual, with help of a low-pass filter;
         a medium-frequency range, within a range from 2 Hz to 40 Hz, which corresponds to cardiac activity of the individual, with help of a band-pass filter; and
         a high-frequency range, within a range from 40 Hz to 500 Hz and beyond, which corresponds to snoring activity of the individual, with help of a high-pass filter; and
      extracting at least one low-frequency range, corresponding to the respiratory activity of the individual, from data coming from the second set of at least one accelerometer.

2. The system of claim 1, wherein:
   the computer is further configured for the calculation of the position of the individual, from data coming from at least one from amongst the first set of at least one accelerometer and the second set of at least one accelerometer; and
   the computer is further configured for determining, based on at least one from amongst the set of given physiological events, a set of at least one cardio-respiratory descriptor of the individual.

3. The system of claim 1, further comprising a microphone;
   wherein the filtering means for filtering the data is further configured for coupling data from the set of at least one gyroscope for measuring angular position with data of at least one from amongst the first set of at least one accelerometer and the second set of at least one accelerometer, for extracting characteristics on position of the individual or on atypical variations in respiratory angular speed; and
   wherein the computer is configured for determining the percentage of snoring per unit time.

4. The system of claim 1, wherein the computer is configured for determining a set of at least one cardio-respiratory descriptor of the individual from amongst:
   an apnea-hypopnea index (AHI),
   a first set of respiratory forces in data coming from the first set of at least one accelerometer,
   a second set of respiratory forces in data coming from the second set of at least one accelerometer,
   a thorax-abdomen desynchronization index, by synchronized comparison of the first set of respiratory forces and of the second set of respiratory forces,
   a heart rate variability (HRV),
   an oxymetric profile or oxygen saturation,
   a respiratory entropy per unit time, and
   a night-time profile of the oxygen saturation.

5. The system of claim 1, wherein the computer is further configured for selecting a set of characteristics, from amongst the set of at least one determined characteristic, by an algorithm of Sequential Feature Selection (SFS) or Fast Correlation-Based Filter (FCBF) type, prior to comparing the set of at least one determined characteristic with the similar characteristics.

6. The system of claim 1, wherein the computer is further configured for calculating at least one from amongst:
- a temporal correlation between at least two events identified over a same range of time or over several ranges of time;
- a set of (event/position) pairs;
- a set of (event/characteristic) pairs;
- a set of (event/characteristic/position) triplets; and
- a set of (event/event/characteristic/position) quadruplets.

7. The system of claim 1, wherein the computer is further configured for identifying a chain of events which, during a predetermined time window, resulted in a cardio-respiratory descriptor of abnormal value.

8. The system of claim 1, further comprising a photoplethysmographic sensor (PPG);
- wherein the filtering means for filtering the data is further configured for averaging data coming from the photoplethysmographic sensor (PPG); and
- wherein the computer is configured for determining thoracic oxygen saturation.

9. The system of claim 1, wherein:
- the low-pass filter is implemented by principal component analysis (PCA) or by discrete Fourier transform;
- the band-pass filter is implemented through adaptive filtering, by envelope extraction, by learning, by cross-correlation, by partitioning into k-averages, or by principal component analysis (PCA); and
- the high-pass filter is implemented by spectral analysis.

10. The system of claim 1, further comprising:
- at least one additional sensor selected from amongst a photoplethysmographic sensor (PPG) and a microphone; and
- a third memory for recording data coming from the at least one additional sensor.

11. The system of claim 10, further comprising:
- means for enabling/disabling the accelerometers and the at least one additional sensor.

12. The system of claim 10, wherein:
- the first memory, for recording the data coming from the accelerometers and from the at least one additional sensor, and the second memory, for recording the reference model, are the same; and
- the first memory, the second memory, and the third memory being either:
  - remote, or
  - connected via a wired data link with the first set of at least one accelerometer, with the second set of at least one accelerometer, and also with the at least one additional sensor.

* * * * *

UNITED STATES PATENT AND TRADEMARK OFFICE
CERTIFICATE OF CORRECTION

PATENT NO. : 11,291,406 B2
APPLICATION NO. : 16/499827
DATED : April 5, 2022
INVENTOR(S) : Damien Colas et al.

It is certified that error appears in the above-identified patent and that said Letters Patent is hereby corrected as shown below:

On the Title Page
In Item (72), Line 2, change "Lyons" to --Lyon--

Signed and Sealed this
Twenty-eighth Day of March, 2023

Katherine Kelly Vidal
*Director of the United States Patent and Trademark Office*